United States Patent [19]

Barnes

[11] 4,329,883
[45] May 18, 1982

[54] APPARATUS FOR COLLECTING DEEP-SEA SEDIMENT PORE WATER

[75] Inventor: Ross O. Barnes, San Diego, Calif.

[73] Assignee: The United States of America as represented by the Secretary of the Navy, Washington, D.C.

[21] Appl. No.: 464,604

[22] Filed: Apr. 26, 1974

[51] Int. Cl.³ .............................................. G01N 1/14
[52] U.S. Cl. .............................. 73/864.52; 73/864.63
[58] Field of Search ............... 73/425.4 R, 425.6, 155, 73/864.52, 864.63

[56] References Cited

U.S. PATENT DOCUMENTS

| 2,625,226 | 1/1953 | Wafford | 73/425.4 |
| 3,095,930 | 7/1963 | Kisling | 73/425.4 |
| 3,245,268 | 4/1966 | Archibald | 73/425.6 |

Primary Examiner—S. Clement Swisher
Attorney, Agent, or Firm—Robert F. Beers; Thomas M. Phillips

[57] ABSTRACT

The collector filters and encapsulates pore water, in-situ, from unconsolidated sediments. A pressure casing mounts a collection cylinder having a valved inlet opening for receiving the sediment pore water through a 1 micron filter. The valve is spring pressed to a closed position and opens in response to hydrostatic pressure. A second valve closes the inlet to the spring-pressed poppet valve. Trigger means initiate the opening of the second valve to expose the poppet valve to the hydrostatic pressure. Preferably, the exposure is accomplished in a delayed manner to assure proper positioning of the sampler before admission of the pore water to the cylinder.

12 Claims, 2 Drawing Figures

APPARATUS FOR COLLECTING DEEP-SEA SEDIMENT PORE WATER

BACKGROUND OF THE INVENTION

The present invention relates to oceanographic sediment-collecting instruments and, in particular, to means for collecting the pore water of deep-sea sedimentary deposits.

During recent years it has become evident that great care must be exercised in the collection and processing of samples of deep-sea sediment pore water. For example, significant concentration changes occur when pore water is removed from core samples at a temperature other than the in-situ temperature. Also, there is the possibility that smaller concentration changes may be due to the effect of pressure on the ion-exchange equilibrium. Usual sampling procedures apparently have precluded thorough investigation of this latter possibility.

The sampling problem is especially serious when the sample is to be used to analyze its dissolved gases. Degassing, bubble formation and atmospheric contamination can and do occur during core recovery and processing and the apparent inability to control these factors probably is the major reason why trace gas analysis of marine sediments still is in its infancy. Previous studies of dissolved gases in sediments have involved core recovery and direct extraction of gases from sediment slurries, see Koyama, (1953) Measurement and Analysis of Gases in Sediment, J. Earth Sci., Nagoya University, 1, 107–118 and Emery and Hogan (1958), Gases in Marine Sediments, Bull. Am. Assoc. Petrol. Geol., 42, 2174–2188. Other procedures involve the initial separation of the pore fluid by a filter press prior to extraction (see Reeburgh) (1968, 1969), Observation of Gases in Chesapeake Bay Sediments, Limnol. Oceanogr., 14, 368–375. Both procedures have utilized a pure gas atmosphere during sample manipulation to eliminate atmospheric contamination and, in doing so, have precluded analyses for that particular gas. Also, despite the use of rather elaborate procedures, the published data suggests sample loss and contamination as well as large variations in replicate analyses that could be the result of sampling problems.

Ideally, the pore fluid should be separated from the solid phase and encapsulated in-situ, thereby eliminating exchange reactions with the sediment and contamination or loss of gases during the recovery and processing. Wilson, Sayles and Mangelsdorf, Jr. (1972) in Trans. Am. Geophys. UN., 53, 529 disclose "An in-situ Filter for Taking Samples of Interstitial Water from Marine Sediments." This sampler stores the fluid in capillary tubing to preserve the filtered fluid in time sequence. Also, it is limited to sampling depths of about 150 centimeters or less below the sediment water interface and, in general, its construction presents other difficulties which have restricted its use.

OBJECTS AND SUMMARY OF THE INVENTION

It is therefore a principal object of the present invention to provide a sampler capable of filtering and encapsulating, in-situ, pore waters of unconsolidated sediments.

Another more specific object is to provide a sampler that is sealed against gas loss and atmospheric contamination so as to permit an analytic precision in the order of ±1% for sampled dissolved gases.

A further object is to provide a sampler capable of filtering the pore water in-situ or in excess of the hydrostatic pressures occuring at oceanic depths.

Still another object relating to the filtering capability of the sampler is to provide a sampler in which the filter element has a low pore volume to surface area ratio and, in addition, a relatively high sample volume compared to the volume of the sea water which fills the filter element and the passageways leading to the sample vessel.

Another more general object is to provide a sampler capable of operating as an outrigger attached to a conventional core barrel.

These and other objects will become more apparent in the ensuing description which is to follow.

In general, the objects are achieved by providing an elongate pressure casing adapted to descend through the sea water and come to rest in a stable position within the sea floor sediment. The casing is provided with a sample collecting chamber and also with a passage communicating its interior with the sediment pore water. Another inlet conduit is formed within the casing to communicate the external passage with the sample collecting chamber and a normally-closed, resiliently-yieldable valve means is disposed in this inlet conduit. Filtering is accomplished by the use of a pore water filter preferably covering the inlet to the external casing passage. Control means, such as a control valve normally block fluid communication between the external passage and the inlet conduit leading to the sample-collecting chamber and special means, such as an externally-operated trigger is provided to activate the control means. Activation of the control means results in exposure of the resilient valve means to surrounding hydrostatic pressure and collection of the sample is achieved by permitting the resilient valve means to yieldably open in response to the hydrostatic pressure. Sealing means are associated with the resilient valve means to assure against gas loss during recovery. Other significant features will be described in detail subsequently.

BRIEF DESCRIPTION OF THE DRAWINGS

The invention is illustrated in the accompanying drawings of which.

DETAILED DESCRIPTION OF THE INVENTION

Figure 1:
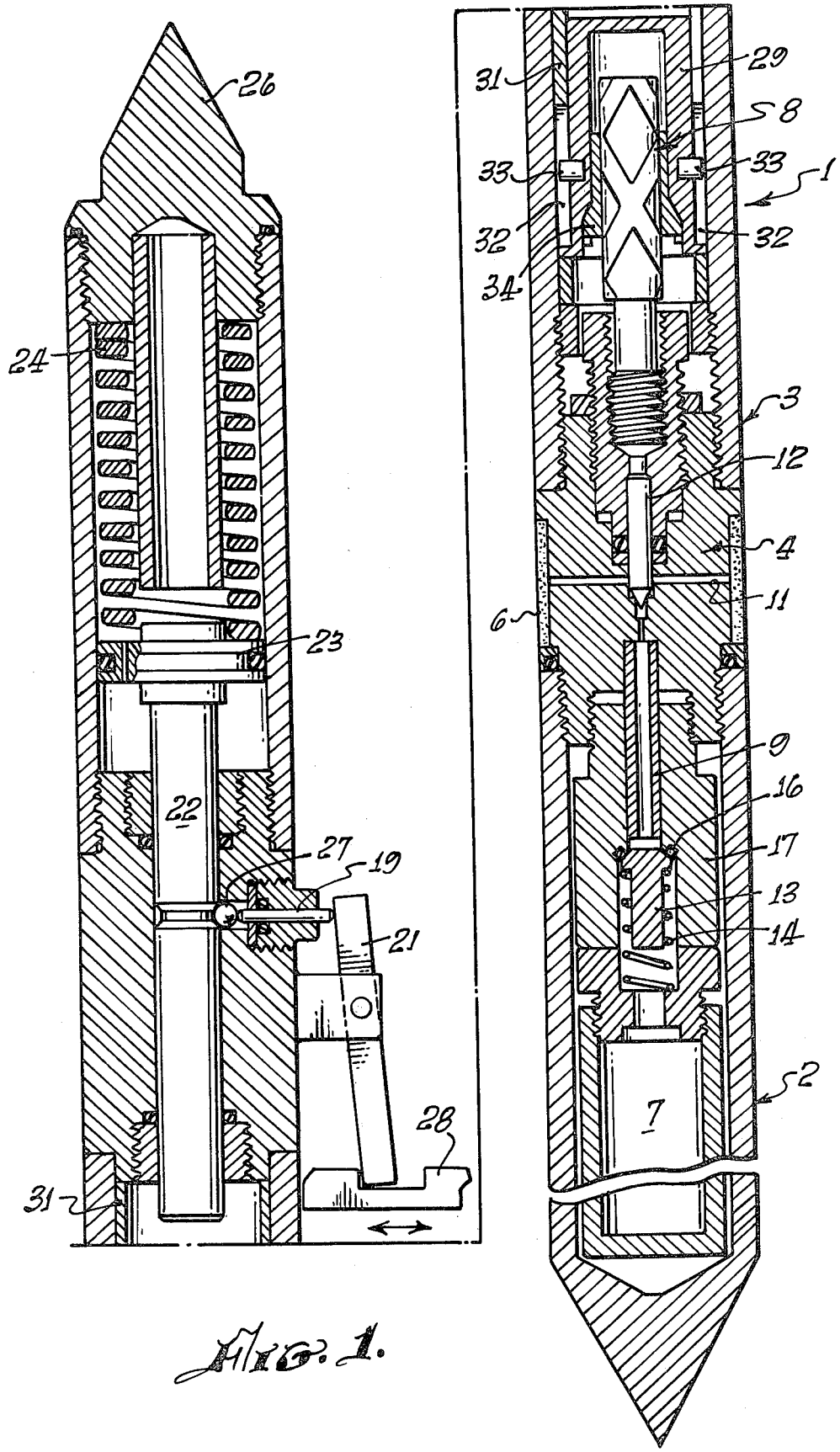
FIG. 1 is a central cross-sectional view showing the assembly of the present apparatus.

Referring to FIG. 1, the present apparatus generally includes a cylindrical elongate pressure casing 1 which, as will be described, is formed of a number of separable parts to permit assembly as well as disassembly for analysis of the collected pore water. The casing, as well as other components, most suitably are formed of materials capable of withstanding the sea water environment as well as the hydrostatic pressures encountered at deep-sea locations and, as will be noted, each end of the casing is provided with a pointed section facilitating descent and lodging in the deep-sea sediment from which the pore water is to be extracted. In use, the apparatus is designed to operate as an outrigger attached to a conventional core barrel or, if desired, it can be mounted on a 2.54 centimeter diameter probe that is driven into the sediment. The outrigger method is preferred because usually a core is obtained to permit complementary studies with the filtered pore water.

For descriptive purposes, it can be considered that the present apparatus is formed of two parts 2 and 3, these parts being separably interconnected by a nut 4 which mounts a special filtering member 6. The mounting of member 6 can be provided in any desired manner. The casing sections 2 and 3 are hollow to receive certain functional components such, in particular, as a stainless steel sample collecting vessel 7 mounted in lower section 2 and a control valve mechanism 8 carried in upper section 3. Collector vessel 7, of course, is the member which receives the sediment pore water and, for this purpose, it is communicated with its sea-floor sedimental environment through an inlet conduit 9 which, in turn, leads into or communicates with transverse or radial passages 11 formed in nut-like member 4. As may be noted, filter member 6 covers the inlet ends of radial passages 11. As also shown, the upper end of inlet conduit 9 normally is blocked or closed by the seating of the lower end of a needle valve stem 12 which, as will be described, forms a part of control mechanism 8. Further, inlet conduit 9 itself is blocked or normally closed by a resiliently-yieldable poppet-type valve 13. Valve 13 is reciprocably mounted in a specially-formed portion of inlet conduit 9, this portion being enlarged radially to receive the valve as well as a spring member 14 which is trapped between flanges of the radially enlarged portion so as to exert a closing, upward pressure on valve 13. Standard buna-N O-rings are used to seal poppet valve 13 so as to prevent leakage across the valve either before or after the pore water has been collected in vessel 7. Since leakage, as will be shown, is a rather critical factor, it is suggested that special low permeability O-rings 16 be used for this purpose. Efficient sealing also is emphasized by the need to evacuate vessel 7 prior to its use in collecting the sample. As may be recognized, poppet valve 13 is a slightly modified version of a commercially-available valve, Nypro #SS-4C2-100.

In use, the apparatus is lowered to the ocean floor and lodged in the sea water sediment. When so lodged, control mechanism 8 is actuated in a manner to be described so as to lift or open valve stem 12 to communicate conduit 9 with radial passages 11. When so communicated, poppet valve 13 is exposed to the hydrostatic pressure of the surrounding water and this pressure causes the poppet valve to yieldably open to admit pore water into sample vessel 7. When vessel 7 is filled or substantially filled, its interior pressure effectively balances the external hydrostatic pressure to permit valve 13 again to close so as to sealably contain the collected sample. The apparatus then is recovered or, in other words, returned to the surface for analysis of the contents of the vessel.

One feature of the present invention is the fact that the contents of vessel 7 remain in a sealed, undisturbed condition until extracted during the analytic procedure. In this regard, the use of poppet valve 13 and the particular construction of inlet conduit 9 assumes significance. In particular, the sample is extracted for analysis by employing a suitable rod to push the poppet valve off of its seat, the rod, most suitably, being attached to the stem of a vacuum bellows valve sealed into a vacuum line of the extraction system. To facilitate the extraction, inlet conduit 9 is formed as an axial, straight-line bore within the casing although, as seen, a portion of the conduit is formed by an elongate neck section 17 threadably secured or otherwise fixed to the top end of vessel 7 and to the lower end of nut-like member 4. The upper portion of inlet conduit 9 is formed by an axial bore 18 provided in nut 4. As will be appreciated, nut 4 would be detached prior to extraction.

Control mechanism 8 is used to lift valve stem 12 and expose poppet valve 13 to the external hydrostatic pressure when the casing is lodged in the sediment. Although this control can be provided in a number of ways, it is preferred to utilize a mechanism which interposes a delay between the time that the mechanism is activated and the time at which the passages to poppet valve 13 are opened. The actuation of the control mechanism normally is responsive to some external force such as a triggering upon impact with the sediment. Such impact triggering can be provided in a number of well-known manners. Presently, it is preferred to employ a mechanism which includes a pin 19 held in a particular disposition by a lever 21 and a pin 28. Such a triggering mechanism is adapted for use with a piston core. When so used, pin 28 is pulled at the time the piston core which carries the present apparatus is released above the sediment. The delay time, which preferably is variable, provides a sufficient interval for the present apparatus to stabilize or come to rest within the sediment.

Considering the control mechanism in greater detail, it will be seen in FIG. 1 that it includes an elongate piston 22 reciprocably mounted within the casing and provided at its upper end with a sealed, radially-enlarged portion 23. A 200 pound die spring 24 is lodged between radially-enlarged portion 23 of the piston and a pointed and threaded closure 26 which forms the upper end of the casing. Spring 24 urges piston 23 in a downward direction from its illustrated, cocked disposition in which it is held by the triggering mechanism. In particular, the shaft of piston 23 is provided with a suitable groove to receive a stainless steel ball 27 and the cocked position is maintained by pin 19 and shaft 21, the pin bearing against ball 27 until shaft 21 of the triggering mechanism is released by a pull upon a lever or pin 28. Spring 24 then forces piston 22 downwardly, although the downward movement of the piston is slowed or restrained by immersing the head or upper portion of the piston in a viscous, silicon fluid which, during the downward movement of the piston is forced through a small, drilled hole 20 of about 0.034 centimeters. The downward reciprocation of piston 22 brings it into engagement with another piston 29, which, as will be explained, forms a part of a so-called 'Yankee' push-type screwdriver mechanism. One important point to be noted is that the lower end of piston 22 normally is spaced a small distance from the upper end of piston 29 to interpose a delay in the actuation of the 'Yankee' mechanism. In general, the operation of the 'Yankee', push-type mechanism is conventional to the extent that due to a high-pitched, threaded engagement, downward movement of piston 29 rotates control valve stem 12 which is part of the mechanism and the rotation causes this valve to lift or open. In particular, piston 29 is reciprocably mounted in a sleeve member 31 that is provided with longitudinal slots 32. Pins 33 carried by piston 29 engage in slots 32 of the sleeve so as to prevent rotation of the piston. Also, piston 29 contains a cross-threaded brass ferrule from a Stanley 'Yankee' #135A spiral ratchet screwdriver and, in the usual manner, the ratchet of the screwdriver permits the ferrule 34 to rotate in one direction only. Since this push-type screwdriver mechanism is a well-known, widely-used tool, it is assumed that its operation will be readily understood without further detailed description.

In operation, sample vessel 7 is evacuated before it is attached to the present sampler and the passageways, such as conduit 9 and passages 11 are flushed with water to eliminate air bubbles. In addition, filter element 6 which covers passages 11 is also flushed with water and the sample vessel valve-filter assembly then is coupled and stored in water until needed. Also, filter element 6 is wrapped with teflon tape to reduce evaporation while the samplers and core equipment are manipulated on the ship. The tape, of course, is removed just before the core enters the water.

The assembly illustrated in FIG. 1 is adapted to be lowered through the sea water from a ship so as eventually to lodge in the sea floor sediment. If used as an outrigger on a piston core barrel, the triggering mechanism for the control mechanism is released at the time the core barrel is released and the delay in the control mechanism permits the apparatus to stabilize in the sediment. Actuation of the control mechanism lifts valve stem 12 to open the communication between the passages 11 and inlet conduit 9 to expose poppet valve 13 to hydrostatic pressure. This external pressure acts against the spring of the poppet valve to yieldably open the valve and, in use, it has been found that customarily an opening pressure of about 2.4 bars to 6.9 bars is needed. The pore water of the sediment then enters vessel 7 after first being filtered through member 6. Preferably, member 6 is a multi-layered filter formed by sandwiching a fine $1\mu$ stainless steel mesh layer between layers of coarse $40\mu$ mesh, the coarse layers providing protection and a support screen so as to allow the flow of fluid beneath the fine mesh filter to the passages leading to vessel 7. This filter element has a low pore volume-to-surface area ratio on the order of 0.017 cm$^3$ for each square centimeter of the external surface area. The total volume of the filter passageways leading to vessel 7 is 0.34 cm$^3$ for a filter area of 11.8 cm$^2$. These dimensions are of some significance since, as will be appreciated, the water in the filter element pore space is assumed to exchange during the sampler descent and to contain bottom water when it reaches the sediment interface. In the analytic procedures the measured gas concentrations should be corrected for the gas concentrations in the water filling the passageways and the filter element. However, in the present apparatus, even large uncertainties in these values result in only small errors for the corrected concentration because the volume involved is small compared to the sample volume.

Figure 2:
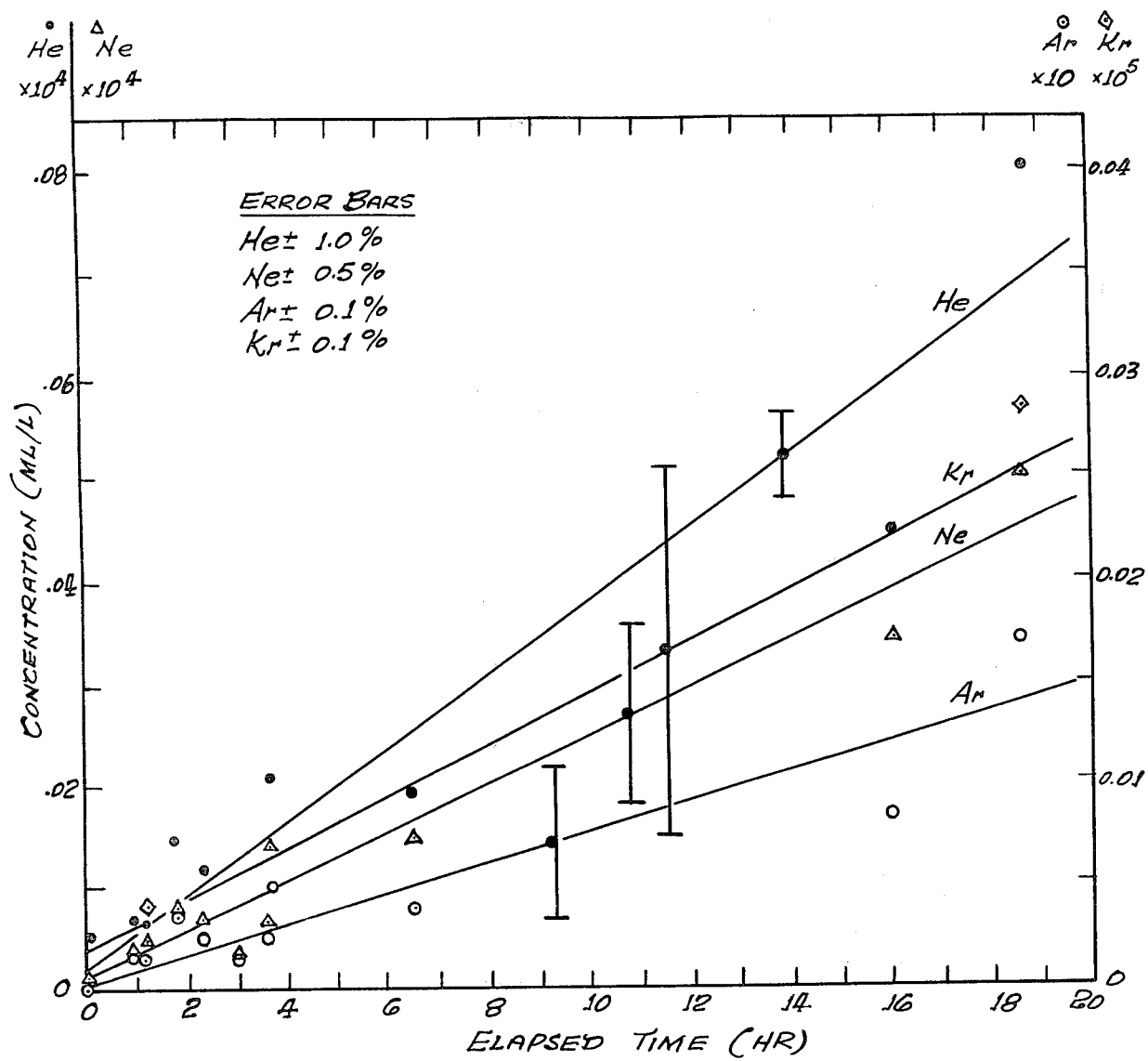
FIG. 2 is a plot illustrating certain leakage characteristics of the present sample cylinder.

Another significant factor involves the spring pressure on poppet valve 13. In particular, this pressure should be sufficient to reduce leakage into the cylinder to very low values. In actual use, the uncertainty in the leakage correction due to residual gas in the cylinder has been found to be quite small after a period of several days. The error in the calculated concentration is plus or minus 1% due to the uncertainty in the leakage correction for helium and much lower for the heavier inert gases that were analyzed. FIG. 2 is a plot illustrating this leakage factor although it should be noted that the data obtained for this figure was obtained with the use of standard buna-N O-rings to seal the poppet valve and that these O-rings were slightly deformed due to previous high pressure sample collection. The use of relatively new low-permeability O-rings is indicated to reduce the leakage factor and its variability. The plot of FIG. 2 shows the gas concentration in the sample cylinders in ml STP/1 volume versus the time elapsed between removal from the evacuating line and mounting on the sample extraction system. During this time, the cylinders were stored under water to simulate actual sampling conditions. The plotting symbols for each gas are shown next to the gas chemical symbol at the top of the figure. The lines or curves were drawn by eye to provide a reasonable fit to the data. However, the lines do not pass through the origin because some leakage on the external O-ring seal occurred after the cylinder was mounted on the extraction system and before the extraction was actually performed. Also, the Kr values have not been corrected for the analytical blanks as is the case with the other gases. The uncertainty in the leakage correction due to the variable leakage rate as shown on the plot is estimated to be 2% for He, $<0.5\%$ for Ne, 0.1% for Ar and $<0.1\%$ for Kr expressed as percent of deep water gas concentrations.

Pressure chamber tests also were conducted to provide data on filtered volume versus hydrostatic pressure, sediment porosity and time. Using such data, it can be decided how long to leave the sampler in the sediment to assure complete filling with the desired pore water. These times are on the order of several minutes using typical clay-rich pelagic surface sediments for filtered volumes of about 10 cm$^3$. The filtered volume versus time data shows that there was little if any drawdown of fluid along the sides of the sampler when the filter element was less than 5 cm below the sediment-water interface. The actua sampling depths usually are much greater than 5 cm below the interface so contamination by drawdown can be neglected upon the assumption that it is quite small or negligible compared to other sources of error.

Another possibility that should be taken into consideration is the fact that the actual filtering process might alter in-situ concentrations. However, it has been shown that filtering pressures well in excess of hydrostatic pressure at oceanic depths (except possibly in trenchs) are required to obtain altered concentrations of ionic species from high ionic strength pore fluids like those in marine sediments. Thus the assumption can be made that the same would be true for neutral dissolved gases unless the measured data might lead one to suspect that this is incorrect.

Bubble formation in the filtered fluid should not occur until the fluid is inside the sample container while it is filling since the fluid in the passageways from filter to container still is pressurized to the opening pressure of the poppet valve. Consequently, degassing or stripping during sampling should not become a problem.

As has been explained, the particular advantages of the present apparatus include the fact that the pore fluid is filtered under in-situ hydrostatic pressure and it is collected in a stainless steel vessel 7 that keeps the sample under pressure and minimizes contamination and loss. Further, the sample need not be touched or exposed in any way until it is mounted on and expanded into the extraction line of the analytical system. As already stated, vessel 7 then is opened directly into the extraction line by pushing the poppet of its seat with a rod attached to the stem of a vacuum bellows valve. However, if desired, a normally-closed needle valve can be provided in the lower end of sample vessel 7 and the extraction can be accomplished through this valve. Such a valve is opened by the pressure of a carrier gas applied to the opened valve 13. One advantage of this type of extraction is that it permits the sample to be analyzed by more conventional gas chromatographic techniques. These advantages, coupled with such others as have been identified, provide an instrument which has been found to be quite useful. Of at least equal significance, use of the present instrument has been most beneficial in permitting studies and investigations which previously were not practical.

Obviously many modifications and variations of the present invention are possible in the light of the above teachings. It is therefore to be understood that within the scope of the appended claims the invention may be practiced otherwise than as specifically described.

I claim:

1. Collector apparatus for collecting deep-sea sediment pore water comprising:
   an elongate casing adapted to descend through said sea water into a stable position within said sediment, said casing being provided with a pore water sample-collecting chamber,
   said casing further being formed with a passage for communicating the casing interior with said sediment pore water and with an inlet conduit communicating said chamber with said passage,
   normally-closed resiliently-yieldable valve means disposed in said inlet conduit,
   control means normally blocking said communications between said passage and said inlet conduit, and
   means for activating said control means, said activation opening said communication for exposing said resilient valve means to the hydrostatic pressure of said deep-sea environment,
   the resilient force of said valve means being such that said valve means yieldably opens with so exposed and closes when the filling of said chamber causes its interior pressure to reach a predetermined level whereby said pore water can be collected in-situ and utilized in a relatively undisturbed condition.

2. The apparatus of claim 1 wherein:
   said control means is a valve means adapted to normally close the inlet end of said chamber conduit, and
   said activating means includes mechanically releasable trigger means for maintaining said control valve means in its normally-closed position, said trigger means releasing in repsonse to external conditions for permitting said valve to open when said collector is stably disposed in said sediment.

3. The apparatus of claim 2 wherein saic control valve means includes normally inactive valve opening means controlled by said releasably trigger means for opening said control valve means, and
   said valve opening means includes mechanical means adapted to delay said activation for predetermined interval immediately following said trigger release, said interval being sufficient to permit said collector to stabilize in said sediment.

4. The apparatus of claim 3 wherein said valve opening means includes,
   a reciprocably-mounted valve-opening piston normally held in a fixed reciprocated position by said trigger means, and
   resilient means reciprocably urging said piston into a valve-opening position,
   said resiliently-responsive piston reciprocation being initiated by said trigger release and including an initial increment of travel prior to reaching its valve opening position whereby said valve opening is delayed.

5. The apparatus of claim 4 further including means for slowing the rate of travel of said piston during said initial increment.

6. The apparatus of claim 4 wherein said claim 4 wherein said piston is adapted to be reciprocably moved into a cocked position maintained by said trigger means.
   said collector casing further being formed by separable parts whereby said piston can be exposed for said cocking movement.

7. The apparatus of claim 1 wherein said inlet conduit extends axially of said elongate casing and said casing passage extends transversely outwardly of said conduit said apparatus further including pore water filter means disposed in said casing passage.

8. The apparatus of claim 7 wherein said axial conduit is formed with a valve seat adapted to be closed by said resiliently-yieldable valve means,
   said valve means further including sealing means for rendering said valve closure gas-tight whereby gases in said collected pore water are retained in said chamber until utilization.

9. The apparatus of claim 8 wherein said pore water filter means is formed as a sandwiched multi-layered member having a fine mesh pore water screen sandwiched between protective filter screens, said sandwiched member being mounted over the inlet end of said transverse passage.

10. The apparatus of claim 8 wherein said resilient force applied to said resiliently-yieldable valve is sufficient to maintain said sealing against atmospheric pressure.

11. The apparatus of claim 10 wherein said collector chamber is in the form of a separably-mounted collector vessel,
    said inlet conduit being fixedly carried by said vessel.

12. The apparatus of claim 11 wherein said casing is formed of separable parts for permitting said inlet conduit to be exposed during said utilization.

* * * * *